Figure 1:
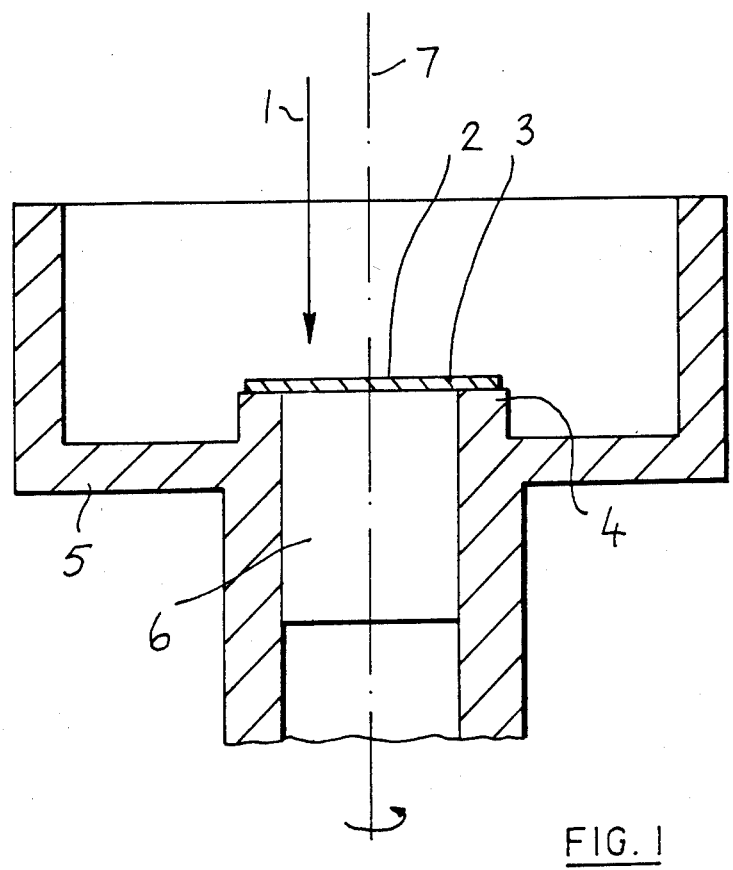

United States Patent [19] [11] Patent Number: 4,500,839
Jones et al. [45] Date of Patent: Feb. 19, 1985

[54] METHOD AND APPARATUS FOR MONITORING WEAR PARTICLES IN A LIQUID MEDIUM

[76] Inventors: David G. Jones, P.O. Box 9531, Dharan, Saudi Arabia; Oh K. Kwon, KIST Labs, P.O. Box 13, Dongdaemum, Seoul, Rep. of Korea

[21] Appl. No.: 396,689

[22] Filed: Jul. 9, 1982

[30] Foreign Application Priority Data

Jul. 9, 1981 [GB] United Kingdom ............... 8121183

[51] Int. Cl.³ ..................... G01N 27/74; G01R 33/12
[52] U.S. Cl. .................................. 324/204; 340/631; 356/72
[58] Field of Search ............... 324/204, 226; 209/222; 356/72, 38, 201–206; 335/305; 340/627, 631

[56] References Cited

U.S. PATENT DOCUMENTS 3,083,830  4/1963  Broderick ........................ 209/222
4,047,814  9/1977  Westcott ........................... 356/72

FOREIGN PATENT DOCUMENTS 52-24573  2/1977  Japan ................................. 324/204

Primary Examiner—Gerard R. Strecker
Assistant Examiner—Walter E. Snow
Attorney, Agent, or Firm—Michael J. Striker

[57] ABSTRACT

An improved method and apparatus of producing Ferrograms in which centrifugal force is used to facilitate the spread of a deposit of magnetically or electrically polarized or polarizable particles onto a substrate to facilitate subsequent analysis of the particles.

15 Claims, 6 Drawing Figures

METHOD AND APPARATUS FOR MONITORING WEAR PARTICLES IN A LIQUID MEDIUM

This invention relates to a method and apparatus for monitoring particles of magnetically or electrically polarised or polarisable particles which are initially suspended in a liquid medium but deposited for monitoring purposes onto a suitable substrate. The invention has particular, but not exclusive, application to the analysis of wear particles in the lubricating medium of an engine or other machine.

It is known (e.g. from U.K. Pat. No. 1415311) that magnetically or electrically polarised or polarisable particles suspended in a liquid medium can be made to deposit on a substrate by flowing the medium over the substrate in the presence of a magnetic or electric force field. Under the correct deposit conditions, which inter alia depend on the medium, the field and the size, density and magnetic or electrical properties of the particles, the particles form a graded distribution on the substrate which facilitates their subsequent examination, e.g. microscopically. Such a prior art graded deposit of magnetic particles is often referred to as a "Ferrogram", the apparatus for producing it as a "Ferrograph" and the science of wear particle analysis using such apparatus as "Ferrography".

A conventional "Ferrograph" uses a slightly inclined stationary flat glass microscope slide to receive the deposit, the liquid medium being allowed to flow under the influence of gravity through an intense magnetic force field from a medium application point located at an upper region of the slide. A substantial proportion (by weight) of the particles deposited in a typical "Ferrogram" remain on the slide close to the application point so that this region can become over congested with particles before desirably dense deposits have formed in lower regions. In general it is the larger particles that deposit first from the flow of medium down the slide adding to the congestion of particles in the vicinity of the application point. Further, to provide a controlled flow of medium over the slide, it is common practice to secure a generally U-shaped barrier on the upper surface of each slide used for a "Ferrogram", the bottom of the "U" passing above the application point and the limbs of the "U" extending down either side of the slide to define the medium flow channel therebetween. The cost of preparation of the barriers represents a significant part of the total cost of "Ferrography".

According to one aspect of the present invention a method of monitoring magnetically or electrically polarised or polarisable particles carried in a liquid medium, comprises impinging a flow of said liquid medium onto the upper surface of a substrate located in a magnetic or electric force field extending generally at right angles to said surface for attracting said particles thereonto, rotating said substrate about an axis, passing through said substrate and disposed generally parallel to said force field, at an angular speed sufficient to cause the rotation to modify the flow speed of said medium across said surface and permit the force field to precipitate said particles onto the surface and optically monitoring said precipitated particles.

According to one way of performing the method, the substrate can be a flat plate of optically transparent material and can be of any convenient shape or size. A square, circular or annular glass plate is preferred for this way of performing the method and a plate 0.1 mm or more thick with a maximum transverse dimension (e.g. diameter) of the upper surface in the range 25 to 50 mm (preferably 30 to 45 mm) is particularly convenient. Where the precipitated particles are to be examined in situ on the substrate it is desirably a transparent sheet of optical quality material (e.g. the sort of glass plate used for a microscope slide).

One particular advantage of the method of the invention is that it can allow the application point of the liquid medium to be extended into a circular application line surrounding the axis of rotation. This effect can be achieved in several ways. For example, the centrifugal force generated by the rotation can be used as the sole transporting force acting on the medium resting on the said surface and in this case the medium would be applied to the substrate between its axis of rotation and its outer edge(s) and will flow radially outwards from the axis, to discharge over the edge(s). The greater the radial distance from the axis to the tube discharging the medium onto the said surface, the more extended the application line will become, but concomitantly the available area of the surface for the collection of precipitated particles will become less for a given area of substrate surface. An annular plate can be used with the application line occurring close to the aperture in the plate.

An alternative way of achieving a circular application line is to use a funnel shaped substrate, and to select the rotational speed of the substrate so that the centrifugal force generated by the rotation is less than the gravitational force caused by the inwardly sloping gradient of the substrate. This alternative way makes the substrates more difficult to fabricate (and thus more expensive) and the control of the method more difficult, but it has the great advantage of permitting the precipitated deposit to overlie substantially the entire upper surface from an application line close to the periphery to the medium discharge at the centre. Further the expansion of the available deposit area is precisely as it is wanted, with the greatest area available for the largest particles first deposited and the smallest area for the hyperfine particles last to be deposited. The semi-angle of the frusto-conical substrate would desirably be in the range 85° to 89°.

A magnetic force field is the norm for wear particle analysis and field strengths in the range 5 to 200 gauss, particularly 10 to 100 gauss, would be typical. A cylindrical magnet axially aligned with the rotational axis of the substrate and disposed just below the latter is a convenient way of obtaining the required force field. The magnet conveniently rotates with the substrate.

The flow rate of the liquid medium onto the substrate can vary widely depending on the viscosity of the medium, the range of sizes of particles to be separated therefrom and the strength of the force field. Typical flow rates would lie in the range 1 to 20 ml/min with the middle of that range being most usual.

The viscosity of the liquid medium will naturally depend on its source, but is not critical. In the case of lubricating oils it could lie anywhere between 1 cSt to 1000 cSt and can be lowered, if desired, with a suitable diluent.

The rotational speed of the substrate can also vary widely depending on circumstances but can easily be optimised. One revolution per second gives satisfactory results for outwardly flowing medium on a flat substrate but speeds between one quarter (15 rpm) and four times (240 rpm) this are contemplated.

To facilitate the optical monitoring, a deposit can be washed with a gentle flow of solvent in the manner well known in conventional "Ferrography", and the rotational speed can be increased to facilitate washing and draining.

According to a further aspect of the invention apparatus for monitoring particles in a liquid medium comprises supply means for feeding medium to a discharge opening thereof, a substrate having a surface disposed below said opening, means to apply a magnetic or electric force field to the substrate so that the field is generally orthogonal to the said surface, and means to rotate the substrate about an axis passing through the substrate and substantially parallel to the force field.

Desirably the supply means does not mechanically compress the fluid medium (e.g. it does not include a peristaltic pump) since this can affect the size and/or shape of the particles.

Other apparatus features can be deduced from the discussion of the method aspect of the invention given above.

Figure 2:
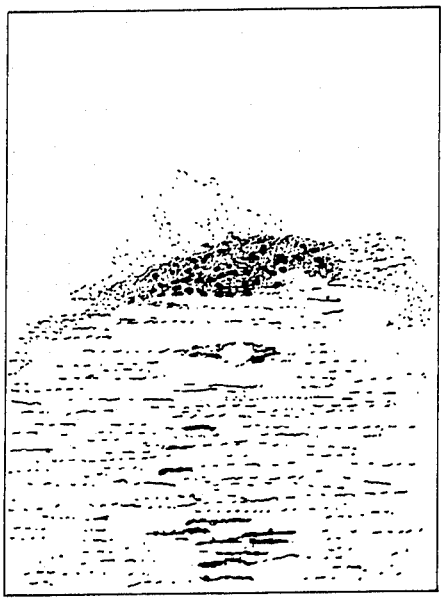
Figure 3:
Figure 4:
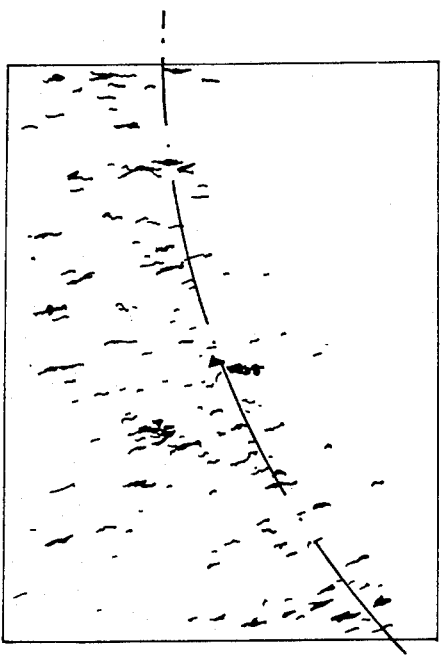
Figure 5:
Figure 6:
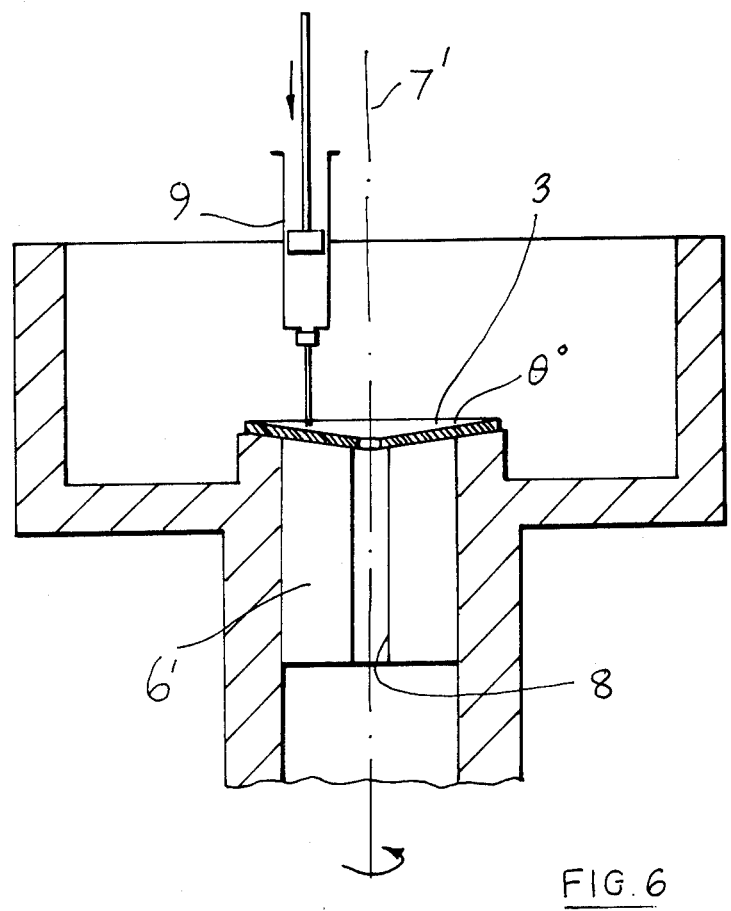

The invention will now be further described, by way of example, with reference to the accompanying drawings, in which:

FIG. 1 is a schematic representation of one embodiment of apparatus according to the invention, FIGS. 2 and 3 are typical "Ferrograms" obtained on a conventional linear, gravity-assisted "Ferrograph" at two different magnifications, FIGS. 4 and 5 are "Ferrograms" obtained on the apparatus sketched in FIG. 1 also taken at two different magnifications, and FIG. 6 is a schematic representation of a second embodiment of the apparatus according to the present invention.

Referring to FIG. 1, a carrier liquid (e.g. an engine lubricant with or without organic diluent) is expelled slowly from a tube 1 onto the flat-horizontal upper surface 2 of a thin glass disc 3 which is sealed in liquid-tight manner to a tubular stem 4 of a rotating assembly 5. The axis of rotation is shown by the dash-dot line 7. The rotational speed is about 1 rev./sec.

Due to centrifugal effects caused by the rotation, the carrier liquid moves radially outwards from its point of application to discharge over the edge of the disc 3 and be collected in the assembly 5.

A cylindrical magnet 6 in the assembly 5 located just below the disc 3 gives rise to a strong field (about 100 gauss) directed upwardly through the disc 3. The magnet 6 rotates with the disc 3. Since the disc 3 overlaps the magnet 6 the peripheral regions of the disc are in a weaker magnetic field than the central region so that there is a magnetic field gradient along each radial path followed by a particle in the carrier liquid from its point of application on the disc 3 to its deposit on the disc.

Particles of different types are deposited at different radial positions, according to their size, density and magnetic susceptibility.

After some 10 ml of carrier liquid have flowed over the disc (typically in a time of two or three minutes), the residual carrier liquid is washed off the disc leaving the particles where they were deposited.

The disc 3 is then removed from the assembly and examined microscopically. The innermost radial deposit is the densest but because it is spread out over a complete circle (e.g. of diameter 10 mm) there is not the congestion known at the application point of a conventional "Ferrogram".

A liquid-tight seal of the disc 3 to the stem 4 is important to prevent carrier liquid (or its particles) staining the underside of the disc. A metal clip, temporary adhesive, rubber ring or partial vacuum can be used to seal the disc in place.

The drive for the assembly can be from above, one side or below.

FIG. 2 is a "Ferrogram" (at ×100 magnification) of a 1 ml sample of synthetic oil from a gear test machine diluted in the ratio 10:1 and FIG. 3 is a further enlargement (at ×400 magnification) of FIG. 2 of an area close to the application point.

It will be noted how congested is the region around the application point and that even on the increased magnification of FIG. 3 it is difficult to separate individual particles from the congested mass of particles. The actual photograph from which FIG. 3 was produced was out of focus over substantial parts of the field of view indicating that the particles of wear debris were piled one on another.

FIG. 4 is a modified "Ferrogram" (also at ×100 magnification) of a similar sample to that used for the production of FIG. 2 this time however the substrate had been rotated at 55 r.p.m. on an apparatus such as that shown in FIG. 1. The line of application of the diluted sample is roughly represented by the chain line in FIG. 4. FIG. 5 is a further enlargement (at ×400 magnification) of a region adjacent to the application line in FIG. 4. The larger particles can be seen to be much more widely distributed and thus easier to analyse.

FIG. 6 shows a second embodiment of apparatus in which a funnel shaped substrate 3' of semiangle $\theta$ is employed over a rotating magnet 6' provided with a bore 8. The carrier liquid, with its entrained particles, is fed to the substrate from a supply means 9 to a region between the outer edge of the substrate 3' and its axis of rotation 7'. The rotational speed is selected relative to the gradient of the substrate 3' so that the liquid, spread out on the substrate is slowed, but not stopped from flowing downwardly to exit through the bore 8. The angle $\theta$ can suitably be in the range 85° to 89°.

What is claimed is:

1. A method of monitoring one of magnetically polarized, magnetically polarizable, electrically polarized and electrically polarizable particles carried in a liquid medium and comprising the steps of:

impinging a flow of the liquid medium onto an upper surface of a substrate located in a magnetic or electric force field respectively, having a component extending substantially at right angles to the surface for attracting the particles thereonto;

rotating the substrate about an axis which passes through the substrate and is disposed substantially parallel to the force field, the force field remaining fixed with respect to the substrate during said rotation instead of having relative motion between the two during the rotation of said rotating substrate, and said rotation being at an angular speed sufficient to modify the flow of the medium across the surface and permit the force field to precipitate the particles onto the surface; and monitoring optically the precipitated particles.

2. The method as defined in claim 1, wherein said impinging step includes impinging the flow of the liquid medium onto the upper surface of the substrate which is a flat plate of optically transparent material and the liquid medium being applied to the substrate between its axis of rotation and its outer edge flows radially outwardly under the influence of centrifugal force generated by said rotating step.

3. The method as defined in claim 1, wherein said impinging step includes impinging the liquid medium onto the upper surface of the substrate located in a magnetic force field having a minimum field strength in the range of 5 to 200 gauss so as to attract the particles onto the substrate.

4. The method as defined in claim 2, wherein said impinging step includes impinging the flow of the liquid medium onto the upper surface of the substrate located in a magnetic force field having a maximum field strength in the range of 5 to 200 gauss so as to attract the particles onto the substrate.

5. The method as defined in claim 1, wherein said rotating step includes rotating the substrate at a speed in the range of 15 to 240 revolutions per minute.

6. The method as defined in claim 2, wherein said rotating step includes rotating the substrate at a speed in the range of 15 to 240 revolutions per minute.

7. The method as defined in claim 3, wherein said rotating step includes rotating the substrate at a speed in the range of 15 to 240 revolutions per minute.

8. The method as defined in claim 1, wherein said impinging step includes impinging the flow of the liquid medium onto the upper surface of the substrate at a flow rate in the range of 1 to 20 ml/minute.

9. The method as defined in claim 2, wherein said impinging step includes impinging the flow of the liquid medium onto the upper surface of the substrate at a flow rate in the range of 1 to 20 ml/minute.

10. The method as defined in claim 4, wherein said impinging step includes impinging the flow of the liquid medium onto the upper surface of the substrate at a flow rate in the range of 1 to 20 ml/minute.

11. The method as defined in claim 1, wherein said impinging step includes impinging the flow of the liquid medium onto the upper surface of the substrate having a frusto-conical configuration sloping downwardly in a radially inwardly direction symmetrically about its axis of rotation and between its axis of rotation and its outer edge thereof, said rotating step including rotating the substrate at a speed selected relative to the gradient of the downwardly sloping surface and the viscosity of the liquid medium so that the liquid medium flows towards the axis of rotation and the particles are precipitated on the substrate radially inwardly of the line of application of the liquid medium on the substrate.

12. The method as defined in claim 10, wherein said impinging step includes impinging the flow of the liquid medium onto the upper surface of the substrate having a frusto-conical configuration with a semi angle in the range of 85°–89°.

13. An apparatus for monitoring particles in a liquid medium and comprising:
 supply means including a discharge opening for feeding the liquid medium therethrough;
 a substrate having an axis and a surface disposed below said discharge opening;
 means to supply a steady magnetic force field to said substrate so that a component of said magnetic force field is disposed substantially orthogonal to said surface of said substrate; and
 means to rotate said substrate while said magnetic force field remains fixed with respect to said substrate during the rotation thereof, said rotation being about said axis passing through said substrate and substantially parallel to said magnetic force field.

14. The apparatus as defined in claim 13, wherein said means to supply said steady magnetic force field to said substrate includes a cylindrical magnet rotating with and disposed closely below said substrate.

15. The apparatus as defined in claim 13; further comprising a rotatable assembly having a central stem and a rotating axis, said substrate being supported centrally of said rotating axis of said rotatable assembly and said magnet being axially aligned with said rotating axis and disposed in said stem.

* * * * *